(12) United States Patent
Mohamed et al.

(10) Patent No.: US 8,361,743 B2
(45) Date of Patent: Jan. 29, 2013

(54) BIOLOGICAL PRODUCTION OF ZEAXANTHIN AND CAROTENOID BIOSYNTHESIS CONTROL

(75) Inventors: Issouf Mohamed, Argyll (GB); Andrew Spragg Mearns, Argyll (GB); Kathryn Fraser, Argyll (GB); Richard Hodgson, Horsham (GB)

(73) Assignee: Aquapharm Bio-Discovery Ltd., Oban (GB)

( * ) Notice: Subject to any disclaimer, the term of this patent is extended or adjusted under 35 U.S.C. 154(b) by 1161 days.

(21) Appl. No.: 11/913,604

(22) PCT Filed: May 5, 2006

(86) PCT No.: PCT/GB2006/001648
§ 371 (c)(1),
(2), (4) Date: Jun. 27, 2008

(87) PCT Pub. No.: WO2006/120400
PCT Pub. Date: Nov. 16, 2006

(65) Prior Publication Data
US 2008/0293097 A1   Nov. 27, 2008

(30) Foreign Application Priority Data

May 7, 2005 (GB) .................................. 0509341.4

(51) Int. Cl.
*C12P 1/00* (2006.01)
(52) U.S. Cl. ......................................................... 435/41
(58) Field of Classification Search ........................ None
See application file for complete search history.

(56) References Cited

PUBLICATIONS

McCammon et al. "Taxonomy of Antarctic *Flavobacterium* species: description of *Flavobacterium gillisiae* sp. nov., *Flavobacterium tegetincola* sp. nov. and *Flavobacterium xanthum* sp. nov., nom. rev. and reclassification of [*Flavobacterium*] *salegens* as *Salegentibacter salegens* gen. nov., comb. nov." Int'l J. of Syst. & Evol. Microb. 2000, 50 1055-1063.*
Hubbard et al. "The Biosynthesis of Prodigiosin, the Tripyrrylmethene Pigment from *Bacillus prodigiosus* (*Serratia marcescens*)" Biochem J. Feb. 1950; 46(2): 220-225.*
Alcantara et al. "Influence of carbon and nitrogen sources on *Flavobacterium* growth and zeaxanthin biosynthesis" Journal of Industrial Microbiology & Biotechnology (1999) 23, 697-700.*
Hosokawa, M., Nishida, K., Sawabe, T., Miyashita, K., Hou, C.T. 2012. "Production and conversion of functional carotenoids by bacteria [abstract]". American Oil Chemists' Society.*
International Search Report and Written Opinion of the International Searching Authority for PCT Application No. PCT/GB2006/001648, mailed Aug. 22, 2006, 2 pgs.
Nedashkovskaya et al., "*Algibacter lectus* gen. nov., sp. nov., a novel member of the family Flavobacteriaceae isolated from green algae," *International Journal of Systematic and Evolutionary Microbiology* 54: 1257-1261 (2004).

* cited by examiner

*Primary Examiner* — Jon P Weber
*Assistant Examiner* — Thane Underdahl
(74) *Attorney, Agent, or Firm* — Myers Bigel Sibley & Sajovec PA

(57) ABSTRACT

The present invention relates to the isolation of carotenoids and in particular the xanthophyll zeaxanthin (zeaxanthin-β, β-Carotene-3,3'-diol) and optionally other carotenoids such as lycopene, β,β-carotene, 3'-hydroxyechinenone β-cryptoxanthin and the colourless carotenoids, phytoene and phytofluene from a marine bacterium belonging to the genus *Algibacter* which is capable of producing the aforementioned compounds. The present invention also provides a strain of *Algibacter* which is capable of producing significant levels of carotenoids, especially zeaxanthin at high purity, as well as methods of using the *Algibacter* strain and uses of the carotenoids produced.

18 Claims, 5 Drawing Sheets

Figure 2a is an HPLC chromatogram (450nm) (Thermoelectron) of mixed crude carotenoids produced by AQP096, showing preference for zeaxanthin production at high purity.
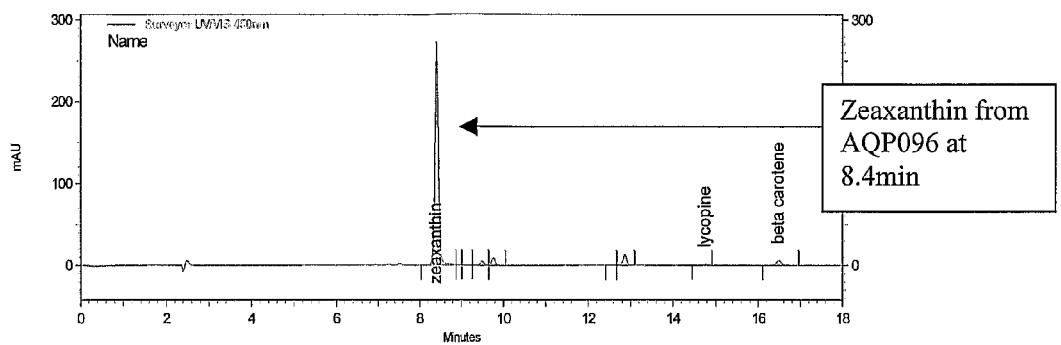
Figure 2b is an HPLC chromatogram of mixed carotenoid standards (450nm).
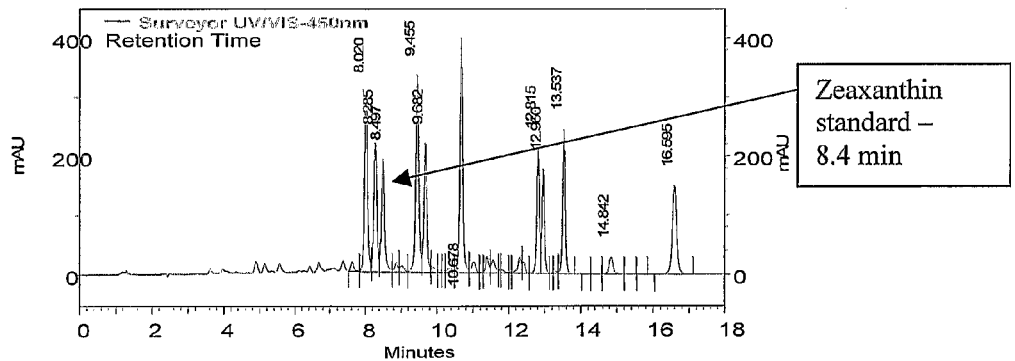

Figure 3: HPLC chromatograms (450nm) of the conversion of zeaxanthin to lycopene using a controlled feed stock ratio of nitrogen and carbon with the addition of carotenoid biosynthetic regulators, imidazole and casamino acid.
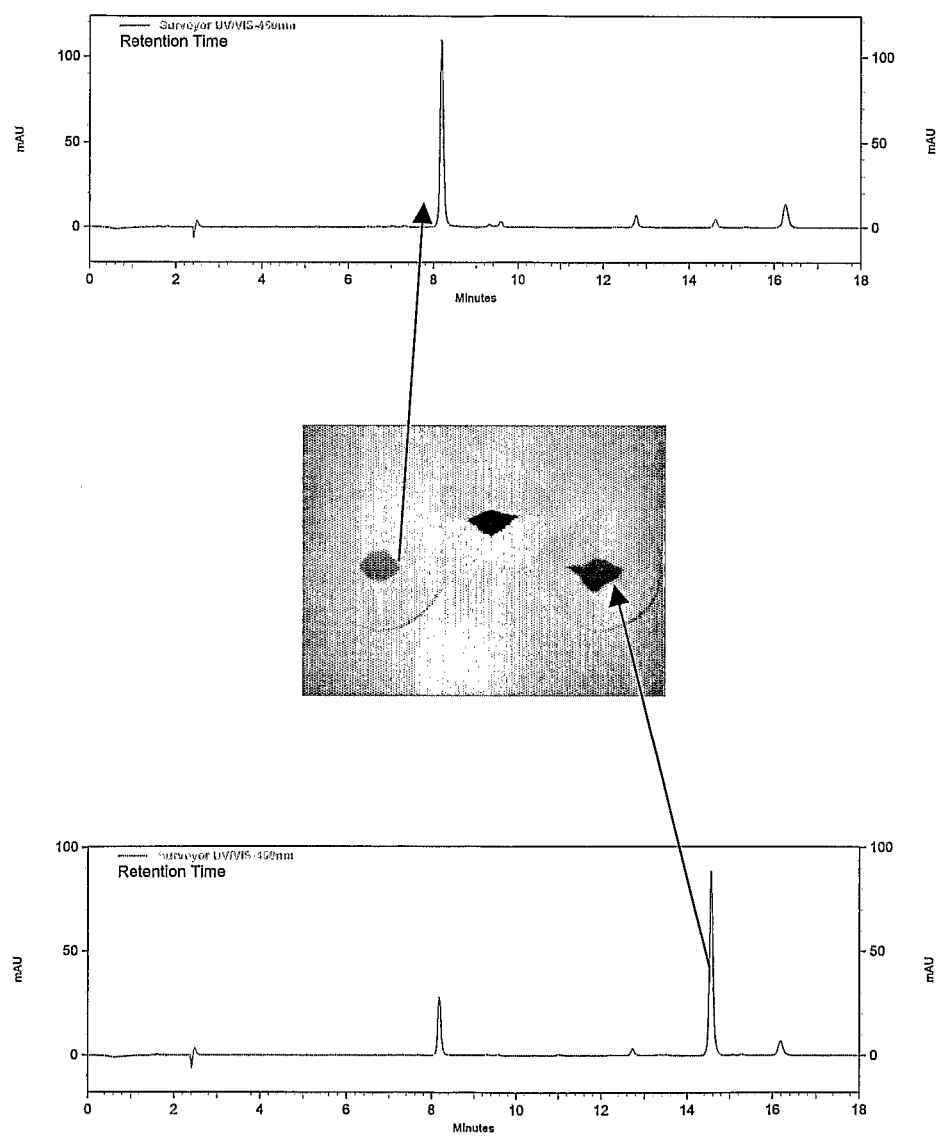

Figure 4a and 4b is an HPLC chromatogram (450nm) of menadione induced carotenoid expression in AQP096
Figure 4a: Control
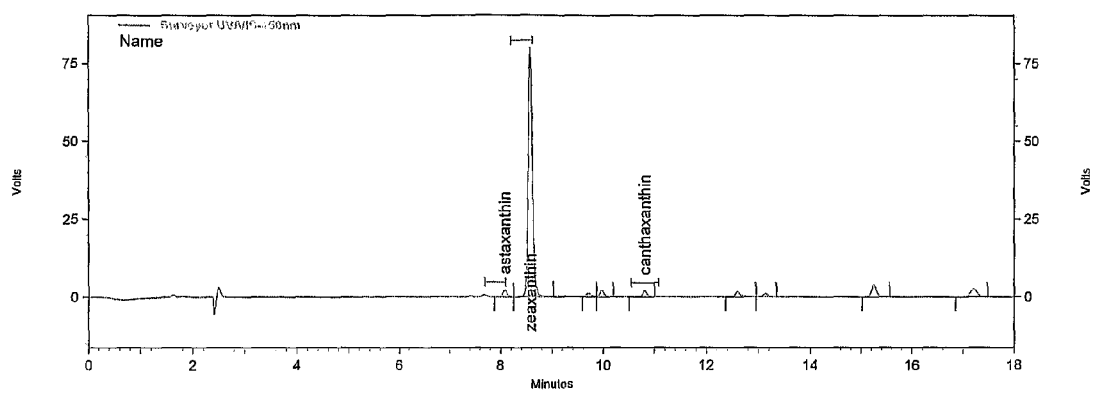
Figure 4b: Menadione induction
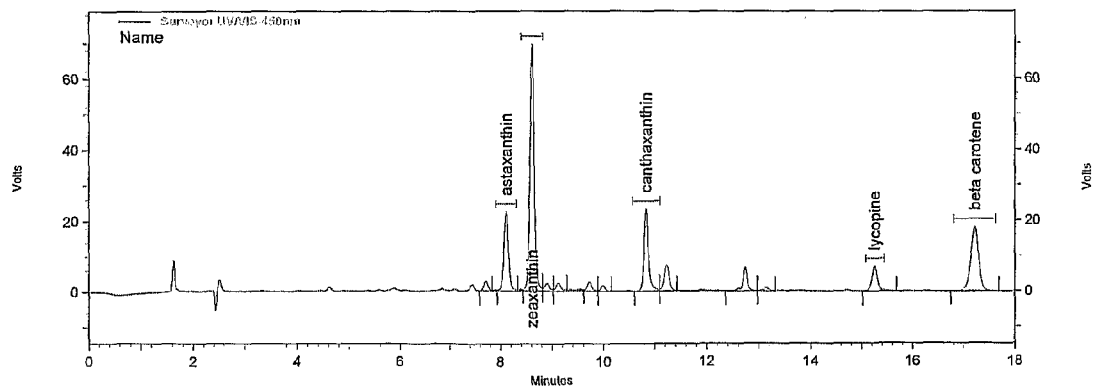

Figure 5: HPLC chromatogram (290nm) of phytoene (9.6min) and phytofluene produced by AQP096.
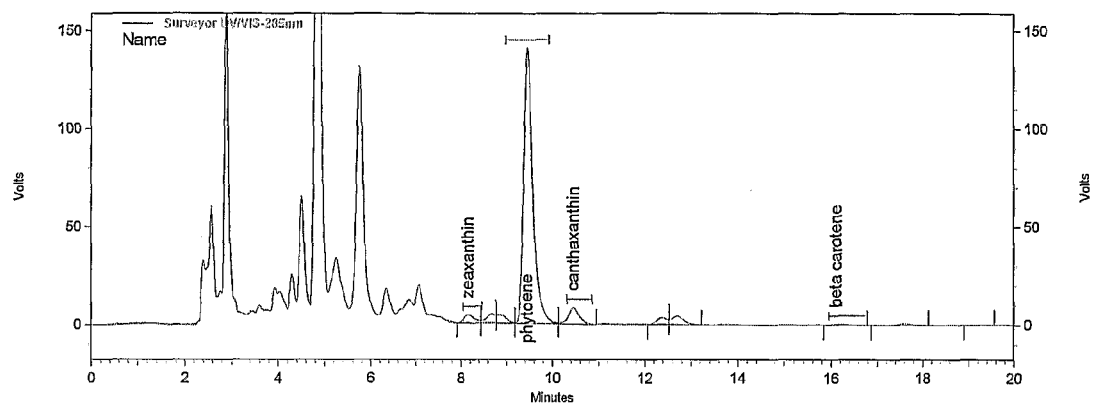

BIOLOGICAL PRODUCTION OF ZEAXANTHIN AND CAROTENOID BIOSYNTHESIS CONTROL

CROSS-REFERENCE TO RELATED APPLICATIONS

This application is a 35 U.S.C. §371 national phase application of International Application Serial No. PCT/GB2006/001648 filed May 5, 2006 which claims the benefit of Great Britain Application No. 0509341.4, filed May 7, 2005, the disclosure of which is incorporated by reference herein in its entirety. The above PCT International Application was published in the English language as International Publication No. WO 2006/120400

FIELD OF THE INVENTION

The present invention relates to the isolation of carotenoids and in particular the xanthophyll zeaxanthin (zeaxanthin-β, β-Carotene-3,3'-diol) and optionally other carotenoids such as lycopene, β,β-carotene, 3'-hydroxyechinenone β-cryptoxanthin and the colourless carotenoids, phytoene and phytofluene from a marine bacterium belonging to the genus *Algibacter* which is capable of producing the aforementioned compounds. The present invention also provides a strain of *Algibacter* which is capable of producing significant levels of carotenoids, especially zeaxanthin at high purity, as well as methods of using the *Algibacter* strain and uses of the carotenoids produced.

BACKGROUND OF THE INVENTION

Carotenoids are an important class of natural fat soluble pigments commonly found in many plants, algae and photosynthetic bacteria, where they play an important role in photosynthesis. Carotenoids can also be found in many non-photosynthetic bacteria, yeasts, moulds and fungi where their role is thought to protect the organism's DNA against photo-oxidation (sun light).

Carotenoids are recognised widely as giving many plants, fruits, flowers and vegetables their red, orange and yellow colours and it is through a diet including such carotenoids that many animals such as salmon, trout and flamingos obtain their flesh and feather colourations. In nature over 620 carotenoids have been identified and characterised.

Carotenoids in animals including humans are widely recognised as having important anti-oxidant activities and some act as a pre-cursor source of vitamin A. There is increasing evidence that some of these play an important role in benefiting human health, and as animals are unable to synthesise these molecules, they therefore must absorb these from the food they eat.

Zeaxanthin (β,β-Carotene-3,3'-diol) is a yellow carotenoid commonly found in maize (*Zea mays*) and is an important carotenoid for eye-health. Zeaxanthin is an important antioxidant found naturally in the retina of humans. It acts as a UV filter to protect the eye against photo-oxidative damage from UV light from the sun. Recent scientific evidence has found that this carotenoid is implicated in reducing the impact of age related macular degeneration (AMD) and cataracts, two of the leading causes of blindness in the world.

Zeaxanthin is also used widely in the agriculture food industry as an agent for pigmenting broiler chickens, the yolks of eggs and is also used as a food supplement by humans to help protect against AMD. It can also be used as a colourant in the cosmetic and food industries.

These dietary pigments such as zeaxanthin are added to feed to aesthetically improve the colouration of chicken products such as egg yolks and the chickens themselves to improve the aesthetic quality of broiler poultry. This is necessary, as in nature these animals are unable to synthesise these products for themselves and must obtain these pigments from their diet.

Zeaxanthin is synthesized naturally by very few bacterial species with the majority belonging to the genera *Flavobacterium* and *Paracoccus*.

The bacterial species *Flavobacterium multivorum* has been described as being able to produce zeaxanthin (U.S. Pat. No. 5,308,759).

The bacterial species *Paracoccus zeaxanthinifaciens* sp. nov has also been described as producing zeaxanthin (Berry et al. 2003).

Apart from bacterial production of zeaxanthin, commercial natural zeaxanthin is mainly provided from marigolds and alfalfa. However, this biological source is associated with stability problems and biological availability when formulated for the poultry industry. There is current work being conducted to improve these qualities from marigold (Bosma et al. 2003). Most marigold products must first be solvent extracted, saponified and require the addition of anti-oxidants in the extraction process. Previous work conducted by Gierhart et al. 1992 have shown that zeaxanthin produced from *Flavobacterium multivorum* is 2-3 times more bioavailable than that extracted from marigold.

Lycopene is an open-chain unsaturated carotenoid that imparts red colour to tomatoes, guava, rosehip, watermelon and pink grapefruit. Lycopene is a proven antioxidant. Antioxidants neutralize free radicals, which may damage the body's cells. Research shows that lycopene in tomatoes can be absorbed more efficiently by the body if processed into juice, sauce, paste and ketchup. The chemical form of lycopene found in tomatoes is converted by the temperature changes involved in processing to make it more easily absorbed by the body.

In the body, lycopene is deposited in the liver, lungs, prostate gland, colon and skin. Its concentration in body tissues tends to be higher than all other carotenoids.

Ongoing preliminary research suggests that lycopene is associated with reduced risk of macular degenerative disease, serum lipid oxidation and cancers of the lung, bladder, cervix and skin.

Studies are underway to investigate other potential benefits of lycopene—including the H.J. Heinz Company sponsored research at the University of Toronto and at the American Health Foundation. These studies will focus on lycopene's possible role in the fight against cancers of the digestive tract, breast and prostate cancer.

The main commercial source of natural lycopene is from tomato and from the fungus *Blakslea trispora*. However, to the best of the inventor's there are no reports of natural lycopene being isolated from a bacterium and in particular from the genus *Algibacter*, in high yields.

Phytoene & phytofluene are colourless precursors in the carotenoid biosynthetic pathway. Beyond being antioxidants, they also have the capacity to fight hydroxyl radicals—the most powerful radicals in nature. They are also said to have an anti-inflammatory action, protecting the skin against inflammation and UV radiation, and can help protect the cardiovascular system by preventing oxidation of LDL. It is anticipated that they will be used in dietary supplements or in any food where an additional health benefit is desirable. Phytoene and Phytofluene have also been seen to work together with other ingredients like CoQ10 and pigmented carotenoids to boost their activity, stabilise these molecules and prevent degradation. Colourless carotenoids are suitable for cosmetics because of their anti-oxidant and anti-ageing properties. It is also judged that it would be easier to develop sales in the cosmetics arena, as colour is particularly pertinent for this market. At present, colourless carotenoids come from specially cultured tomatoes and algae.

An object of the present invention is to provide an alternate higher purity source of natural zeaxanthin, lycopene and colourless carotenoids desirably phytoene and phytofluene, optionally including phytoene, phytofluene, lycopene, β,β-carotene, 3'-hydroxyechinenone and β-cryptoxanthin derived from marine bacteria, belonging to the genus *Algibacter*. A further object is to provide a bacterium belonging to the genus *Algibacter*, capable of producing zeaxanthin at high purity e.g. greater than 98% total carotenoids.

SUMMARY OF THE INVENTION

In a first aspect there is provided a method for producing at least one pre-carotenoid and/or carotenoid orange compound, comprising the steps of:

a) culturing bacteria from the genus *Algibacter* sp. in a suitable culture medium under conditions and for a time period suitable for production of said pre-carotenoid and/or carotenoid compound(s); and b) recovering said pre-carotenoid and/or carotenoid compound(s) from the bacteria.

The pre-carotenoid compounds may be essentially colourless, but the carotenoid compounds may display a yellow/orange pigment which may aid purification. The method may further comprise the optional steps of:

c) optimising the fermentation and culture conditions for maximum cell biomass and/or pre-carotenoid and/or carotenoid production;

d) conducting classical strain mutagenesis on bacterial strain AQP096 to identify over producing colourless pre-carotenoid and/or orange carotenoid mutant strains;

e) altering said conditions by controlling the ratio of carbon to nitrogen feed stock with the addition of carotenoid biosynthesis regulators to control pre-carotenoid and/or carotenoid biosynthesis; and/or f) altering said conditions with the addition of menadione so as to increase expression of one or more of the carotenoid biosynthetic pathway compounds.

It is understood that the colour of the yellow/orange pigmented compound may vary considerably but may generally vary from a light yellow to orange/pink/red colour. For example, the fractions that comprise carotenoids may be characterised by a generally orange colour.

Bacteria from the genus *Algibacter* sp. may be any *Algibacter* species which displays a yellow, orange or pink red pigment on growth. Preferably the Algibacter species is a marine bacterium and may require NaCl for growth. Preferably the *Algibacter* species produces zeaxanthin and or lycopene (dependent on culture conditions) as the major carotenoid. It is understood that other carotenoids such as phytoene and phytofluene may be found in minor proportions. That is, the Algibacter species utilised should desirably produce zeaxanthin and/or lycopene in a greater proportion than any other carotenoid. Typically zeaxanthin and/or lycopene will be produced in an amount of at least 40%, 50%, 60%, 70%, 80%, 90% or 98% of the total carotenoids produced and dependent of the fermentation conditions used to culture the *Algibacter* strain. Preferably, the marine bacterium belonging to the genus *Algibacter* species is strain AQP096 as deposited in accordance with the requirements under the Budapest Treaty at the National Collections of Industrial, Food and Marine Bacteria (NCIMB) having an address of NCIMB Ltd., Ferguson Building, Craibstone Estate, Buckburn, Aberdeen AB21 9YA on 12 Apr. 2005 under accession number NCIMB 41268 or a mutant or variant thereof having the property of producing yellow-pigmented and/or orange pigmented compounds respectively, e.g. the property of producing at least one carotenoid, such as zeaxanthin and or lycopene. One such mutant is AQP096 MU016 as deposited in accordance with the requirements under the Budapest Treating at the NCIMB on the 6 Apr. 2006, under accession number NCIMB 41383.

Desirably the yellow/orange/pink red-pigmented compound(s) are carotenoids, such as zeaxanthin, 3'-hydroxyechinenone, β-cryptoxanthin, lycopene and β,β-carotene. Such carotenoids may be recovered in substantially isolated form, or as a mixture of carotenoids. Preferably the carotenoid is zeaxanthin or lycopene or a mixture thereof which is/are recovered in a substantially isolated form. Desirably the colourless compounds are pre-carotenoids, such as phytoene and phytofluene.

Suitably the bacteria may be cultured in media comprising an assimible carbon source, such as a carbohydrate, and at least one source of assimible nitrogen source, such as amino acids. Desirably the media comprises additional trace elements such as mineral salts especially NaCl, vitamins etc. One suitable media is Difco 2216E Marine Broth or variants thereof. Another suitable media is 0.3-3% peptone, e.g. 0.5% peptone and 0.05-0.75% (e.g. 0.1%) Yeast Extract source in purified seawater (natural). More preferably, more suitable media for the increased production of cell mass utilises 3% Peptone+4% Yeast Extract+0.5% Thiamine in filtered seawater incubating for 48 hrs (See table 4). The skilled addressee will appreciate that fermentation and growth of the bacteria may be optimised to provide desired biomass production using varying concentrations of the carbon/nitrogen sources such as peptone or glucose and yeast extract in purified seawater. Typically the bacterium may be cultured at 20° C.-27° C. for 24-144 hours shaking at, for example, 120 rpm. More typically the bacterium is cultured for 48 hours at 26° C., shaking at 120 rpm. The pH for the culture is typically pH 7.0-8.0, e.g. 7.2-7.8. However according to the present invention, the preferred medium has the following composition:

| Composition | g/l & μg/ml |
| --- | --- |
| Nitrogen source | 30-50 e.g. 45 |
| Carbon source | 25-40 e.g. 33 |
| Phosphate & Sulphate | 1-5 e.g. 2.5 |
| Fat source | 100 μL/ml |
| Carotenoid biosynthesis regulators* | 20 mMOL |
| Sea water | remainder |

Sources of assimilable nitrogen include but are not limited to numerous substances of animal, vegetable, microbial origin as well as inorganic nitrogen compounds. Among the preferred assimilable nitrogen sources are soya meal, peptone, yeast extract, corn steep liquor, fish meal, meat meal, amino acids, ammonium salts (such as ammonium phosphate and or ammonium sulphate). The most preferred assimilable nitrogen source is corn steep liquor because of low cost of the raw material.

Sources of assimilable carbon include, but are not limited to sugars and their polymers, such as starches, maltose, lactose, glucose, fatty acids and polyalcohols. Preferred carbon sources include corn, corn flour, starch, glucose feed, lactate and acetate. The most preferred assimilable carbon source is corn flour because of low cost of the raw material. To one skilled in the art, corn flour and starch require treatment with enzymes such as α-amylase (commercially available under Termamyl 120 L), which hydrolyses starch to dextrin.

The nutrient media may also contain growth factors such as yeast extract, trace elements originating from organic ingredients. Such ingredients include but are not limited to, phosphorus, sulphur, vitamins. The most preferred growth factors yeast extract combines with low levels of ferrous sulphate and disodium phosphate.

The fat source includes but is not limited to vegetable oil, soybean oil, soap stock and olive oil.

The nutrient media may also contain certain carotenoid biosynthesis control factors such as imidazole and casamino acid. When added to a culture media with a high yeast extract to glucose nutrient ratio, causes the inhibition of the enzyme β-carotene cyclase to accumulate the production of the pink red pigment lycopene from cultures of *Algibacter* sp. AQP096 instead of zeaxanthin.

The yellow, orange, pink red-pigmented compound(s) of the present invention may be generally isolated and purified from the cells of the culture. Namely, microbial cells are separated from the culture by a conventional means such as centrifugation or filtration, and the cells lysed and the pigmented compound(s) subjected to an extraction with a solvent. A small amount of the pigmented compound(s)/carotenoids and colourless compound(s)/pre-carotenoids may be dissolved in a supernatant or filtrate, and the pigment/carotenoids also may be recovered from this. As a solvent for the extraction, any substance in which the pigmented compound(s) is soluble can be used. For example, organic solvents such as acetone, chloroform, dichloromethane, hexane, cyclohexane, tetrahydrofuran, methanol, ethanol, isoproppanol, benzene, carbon disulfide, diethyl ether etc. are used, and preferably tetrahydrofuran is used. The purification can be carried out by conventional procedures such as absorption, elution, dissolving in appropriate solvents and the like, alone or in combination.

According to the present invention, in many cases, zeaxanthin, lycopene, β,β-carotene, 3'-hydroxyechinenone, β-cryptoxanthin, phytoene and phytofluene are simultaneously produced and present in a culture product. Accordingly, in an embodiment of the present invention, any one of the abovementioned carotenoids can be singly obtained by the abovementioned procedure. Alternatively, a mixture of the carotenoids also can be obtained. In this way, the process for carotenoid production of the present invention includes a process for production of an individual carotenoid and a process for production of a mixture of the carotenoids.

The mixture of carotenoids can be separated from each other according to a conventional procedure for mutual separation of carotenoids, such as adsorption/elusion column chromatography, differential extraction, counter current extraction, differential crystallization, etc. Chromatography techniques may include HPLC techniques e.g. normal or reverse phase HPLC.

In addition, for preferential production of an individual carotenoid, or enhanced amounts of carotenoids the desired carotenoid(s) may be preferentially produced by controlling medium composition, culture conditions and the like.

For example, a ratio of carotenoids produced can be changed by changing an aerobic condition. For example, a ratio of carotenoids produced may be changed by an amount of a medium and/or a rate of shaking in flash-shaking culture, and/or by changing a rate of air supply or a rate of agitation in aeration/agitation culture.

Alternatively, or additionally for preferential and/or enhanced production of a particular carotenoid, a *Algibacter* bacterial species can be improved by a mutation such as artificial mutation of, for example AQP096 as described herein so that a mutant *Algibacter* strain preferentially produces and/or produces enhanced levels of desired carotenoid among others. Such mutation treatments include, for example, physical methods such as X-ray radiation, UV radiation and the like; chemical methods such as the use of N-methyl-N'-nitro-N-nitrosoguanidine (NTG), ethylmethane sulfonate (EMS); and biological methods such as gene recombination techniques, or phage exposure techniques known in the art. Processes for production of the carotenoids using such an improved mutant is included in the present process for production of carotenoids.

In a further aspect the present invention also provides a marine bacterium belonging to the genus *Algibacter* sp that produces carotenoids such as zeaxanthin, lycopene, 3'-hydroxyechinenone, β,β-Carotene, β-cryptoxanthin, phytoene and/or phytofluene. Desirably, said bacterium is isolated from other bacterial species and is in purified form. Advantageously, zeaxanthin is the major carotenoid produced (e.g. 40%, 50%, 60%, 70%, 75%, 85%, 90%, 98%) by, for example, the strain *Algibacter* AQP096 (accession number NCIMB 41268 as deposited under the requirements of the Budapest treaty at the NCIMB on the 12 Apr. 2005 or AQP096 MU016 as deposited in accordance with the requirements under the Budapest Treaty at the NCIMB on the 6 Apr. 2006, under accession number NCIMB 41383) which is beneficial in terms of its purification and manufacture. Conveniently said bacterium is cultured in vitro to permit easy harvesting of the required compounds.

The extracted zeaxanthin, lycopene and whole cell product containing mixed carotenoids namely, zeaxanthin, lycopene, cryptoxanthin, 3'-hydroxyechinenone, β,β-carotene, phytoene and/or phytofluene produced by the marine bacterium isolated from the cells may be used in a variety of ways. The zeaxanthin or lycopene either in its isolated form or as a mixed pigment product containing mixed carotenoids may be added to, for example, animal feed where pigmentation is necessary for colouring the yolks of eggs and the skin in of broiler chickens, healthcare for use as an anti-oxidant to help protect the human eye against UV damage and Age Related Macular Degeneration (ADM) (pharmacological) and as an environmentally friendly or as a more bio-available form compared to current synthetic and natural derivatives. Zeaxanthin in its isolated form or as a mixed carotenoid product containing zeaxanthin, lycopene, β,β-carotene, β-cryptoxanthin, 3'-hydroxyechinenone, phytoene and/or phytofluene is extracted from a suitable marine bacterium especially an *Algibacter* strain, such as *Algibacter* AQP096 or AQP096 MU016 may also be formulated as an oil matrix such as sources of omega 3 and omega 6 fatty acids incorporated into a coating, such as cellulose/gelatin capsule. This encapsulated product could be used as in the food-supplement industry (functional foods) as an antioxidant.

The colourless compound(s)/pre-carotenoids phytoene and phytofluene can be used in the cosmetics industry in skin care where a colourless trait is desirable. Beyond being antioxidants, phytoene and phytofluene have the capacity to fight hydroxyl radicals—the most powerful radicals in nature, stronger than free radicals. They are also said to have an anti-inflammatory action, protecting the skin against inflammation and UV radiation, and can help protect the cardiovascular system by preventing oxidation of LDL. They can be used in cosmetics, dietary supplements or in any food where an additional health benefit is desirable and colour is an issue. These products can also be used to enhance shelf life of foods.

In addition to their own health properties, Phytoen and Phytofluen have been seen to work together with other ingredients like CoQ10 and pigmented carotenoids to boost their activity, stabilise the molecules and prevent degradation.

The zeaxanthin and mixed carotenoid pigments as previously described produced by the marine bacterium *Algibacter* sp such as *Algibacter* sp nov AQP096 or AQP096 MU016 may alternatively be used as an environmentally friendly substitute for use in a variety of industrial and consumer markets including paints and coatings, plastics, spin dried fibres, construction materials, paper, ceramics, opt-electronic devices, elastomers, inks, textiles, glass, food products including confectionary, pharmaceuticals and cosmetics.

Alternatively, the zeaxanthin and mixed carotenoid product may be used to promote a pharmacological or physiological effect in animals and humans or as an anti-oxidant for use in the treatment and prevention of disease such as Age Related Macular Degeneration (AMD) and certain cancers.

The present invention also allows the isolation of the genes encoding the enzymes responsible for producing the red-pigmented compound(s) of the present invention as produced by the *Algibacter* sp. strain AQP0960R AQP096 MU016 as described herein. FIG. 1 shows a proposed pathway for the production of zeaxanthin from *Algibacter* AQP096. This pathway may be similar or identical in other *Algibacter* species. The genes necessary for carotenoid production may easily be identified and isolated using general molecular biological techniques known in the art (see for example Sambrook J et al. 2000. Molecular Cloning: A Laboratory Manual (Third Edition) Cold Spring Harbor Laboratory Press. For example, the genes may be identified by hybridisation studies of the genome from the aforementioned *Algibacter* AQP096. Many carotenoid biosynthetic genes/proteins have been identified previously, see for example U.S. 60/434,618 and U.S. 60/435,612, and the known sequences can be used to clone the corresponding genes from *Algibacter*, especially *Algibacter* AQP096 or AQP096 MU016. Typically fragments or oligonucleotides designed against the previously known carotenoid sequences can be used in hybridisation or PCR reactions well known to those skilled in the art to identify and thereafter clone the corresponding *Algibacter* genes/proteins.

The present invention will now be further described with reference to the figures which show:

FIG. 2a is an HPLC chromatogram (450 nm) (Thermoelectron) of mixed crude carotenoids produced by AQP096 showing preference for the production of zeaxanthin; and FIG. 2b is an HPLC chromatogram of mixed carotenoid standards (450 nm).

FIG. 3 show HPLC chromatograms (450 nm) of the conversion of zeaxanthin to lycopene using a controlled feed stock ratio of nitrogen and carbon with the addition of carotenoid biosynthetic regulators, imidazole and casamino acid.

FIGS. 4a and 4b is an HPLC chromatogram (450 nm) of menadione induced carotenoid expression in AQP096

FIG. 5 is an HPLC chromatogram (290 nm) of phytoene and phytofluene produced by AQP096.

DETAILED DESCRIPTION

Example 1

Figure 1:
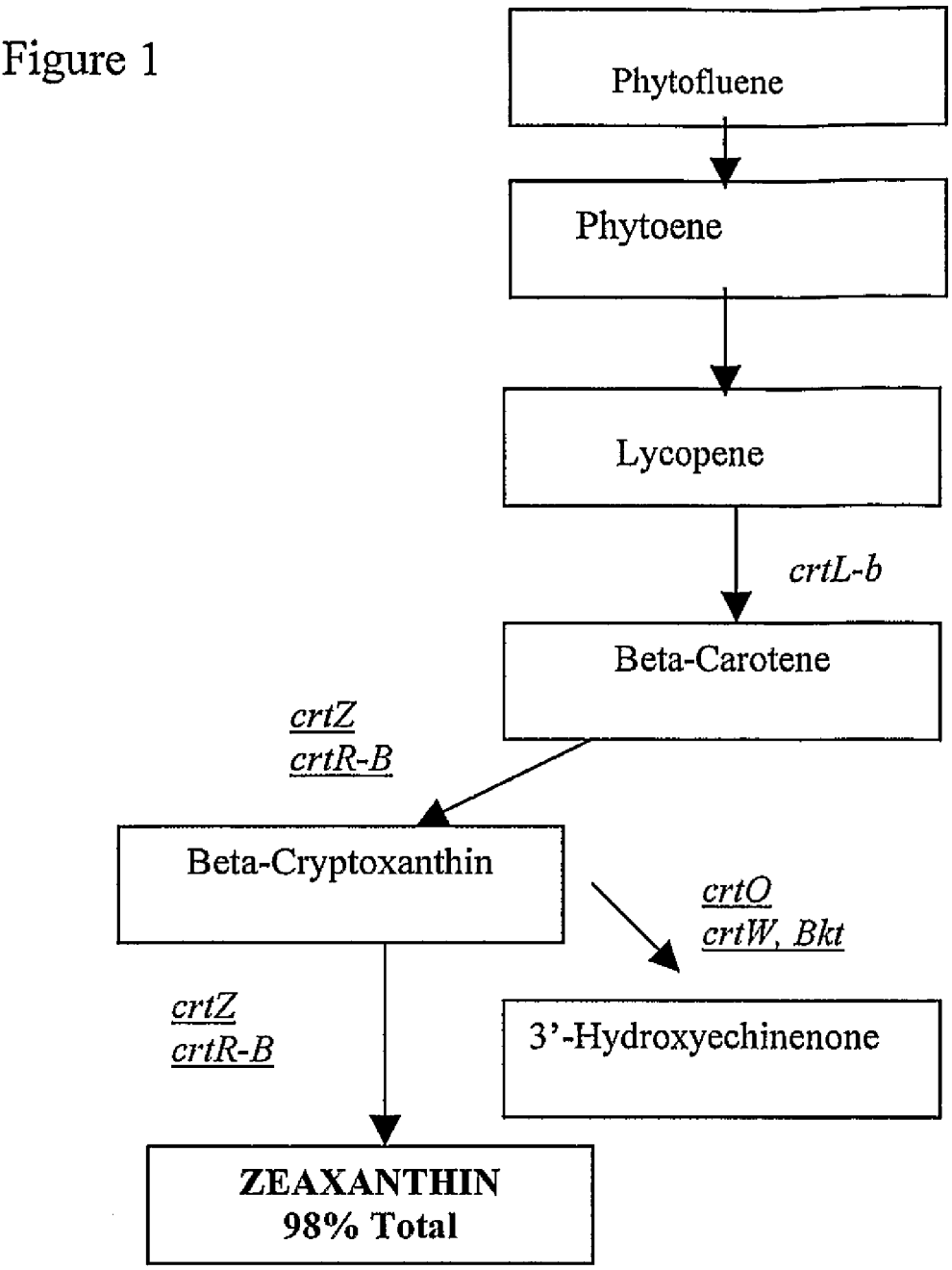
FIG. 1 shows the proposed Genetic Pathway for the production of zeaxanthin from AQP096.

Isolation of *Algibacter* sp. nov Strain AQP096 NCIMB 41268

Seawater samples was collected from several shallow water locations for locating bacteria. 100 ul of seawater were plated out onto Difco Marine Agar 2216E. The agar plates were incubated for 7 days in laboratory ambient conditions (approx 21° C.).

Colonies that displayed shades of yellow, red and orange were sub-cultured and purified resulting in the isolation of particular strains. One of these strains that displayed an yellow-orange shade was chosen (named AQP096) and has been deposited at NCIMB under accession number NCIMB 41268.

Strain AQP096 exhibited a strong yellow-orange pigment on agar medium and when cultured in marine broth produced yellow-orange pigments. The microorganisms are Gram negative rods. The yellow/orange pigment extracted from *Algibacter* sp. AQP096 produced a similar absorption spectra and chromatographic retention time to that reported for zeaxanthin as its major pigment (98%).

On the HPLC using a reverse phase Gemini C-18 250×4.6 mm column, 10 µl of pigment sample was eluted with a linear gradient from 10% v/v Acetone in Water: 100% Acetone (30:70) to 10% v/v Acetone in Water:100% Acetone (5:95) for 10 min followed with a 6 minute run of 10% v/v Acetone in Water:100% Acetone (5:95) before returning to the start conditions of 10% v/v Acetone in Water: 100% Acetone (30:70) with a 1 min linear gradient and a two minute run of 10% v/v Acetone in Water:100% Acetone (30:70) at a flow rate of 1.3 ml/min. Detection was at 450 nm.

The mixed crude carotenoids from AQP096 were compared to mixed carotenoid standards on HPLC (see FIGS. 1a and 1b) and shows similarity to these standards.

The strain was submitted in confidence to an independent laboratory for 16S rRNA molecular analysis and taxonomic work up. The laboratory concluded that the culture was not similar to previously described zeaxanthin producing microorganisms. The culture strain was characterised as an *Algibacter* sp. This is the first report of zeaxanthin production by this genus.

Example 2

Cultivation of *Algibacter* sp. nov and Quantification of Zeaxanthin Production

The liquid medium has the following composition per L of broth

| composition | g/l |
|---|---|
| Yeast Extract | 45 |
| Glucose | 33 |
| Phosphate & Sulphate | 2.5 |
| Fat source | 100 µL/ml |
| Carotenoid biosynthesis regulators* | 20 mMOL |
| Sea water | remainder |

This nutrient medium was adjusted to a pH of 7.5 using a 1M sodium hydroxide (NaOH) solution. The growth conditions for the inoculated cultures at 25° C., pH7.5, for 2 days with continuous aeration. Aeration was provided by shaking at 200 rpm using 25 ml shake Erlenmeyer flask culture.

To extract pigment from *Algibacter* sp, the cell pellet was freeze dried and then resuspended in 100 µl of lysozyme lysis buffer (50 mmol/l Tris, 200 mmol/l NaCl and 0.2 g/l lysozyme, adjusted to pH 7.5 using 1M HCl) in a microcentrifuge tube and left for 45 min in the dark.

A solution of tetrahydrofuran containing 0.05% w/v BHT was prepared and 500 µl was added to the resuspended biomass. This mixture was left for 45 minutes in the dark to extract any carotenoids into the solvent phase.

The sample was then centrifuged (11000 rpm for 3 min) to separate solvent phase, aqueous phase and cell debris. The solvent phase was removed and filtered through a 0.22 μm PVDF filter. The resulting filtrate was then ready for analysis by HPLC and spectrophotometer analysis.

Carotenoids in solution obey the Beer-Lambert law, that is, their absorbance is directly proportional to concentration. According to the "Harvest-Plus handbook for Carotenoid Analysis", Delia et al. the total carotenoid content can be estimated using the following formula:

Total carotenoid content (μg/g):

$$\frac{A * \text{volume(ml)} * 10^{\wedge}4}{\varepsilon * \text{sample weight(g)}}$$

Where A=absorbance
Volume=total volume of extract
$\varepsilon$=absorption coefficient of Zeaxanthin A UV-VIS spectrometer (Cecil 3000 series, scanning spectrophotometer) was used to measure the absorbency of carotenoid samples from strain AQP096 measuring at a wavelength of 450 nm. (A sample of THF+BHT was used as a blank control).

TABLE 1

Total carotenoid content from samples of AQP096

| sample | Optical density | Dilution | Concentration (mg/g) |
|---|---|---|---|
| 1 | 0.855 | 1/6 | 3.288 |
| 2 | 0.698 | 1/8 | 3.579 |
| 3 | 0.356 | 1/16 | 3.651 |

The results in table 1 need to be adjusted for the purity of zeaxanthin produced in the carotenoid crude extract at about 98% of the total carotenoid content.

TABLE 2

Concentration of zeaxanthin adjusted to reflect the purity level of zeaxanthin produced by this strain at 98%

| Sample | Total carotenoid Concentration (mg/g) | Zeaxanthin estimation (mg/g) |
|---|---|---|
| 1 | 3.288 | 3.13 |
| 2 | 3.579 | 3.40 |
| 3 | 3.651 | 3.47 |

From these results, the concentration of zeaxanthin produced by a wild type strain of *Algibacter* sp. AQP096 was 3.47 mg/g of dry biomass.

Example 3

Optimisation of Culture Conditions

The following experiment determines the best set of culture conditions for optimised production of microbial biomass from fermentation of *Algibacter* sp. Media as described in Table 3 were formulated, autoclaved, cooled and inoculated with a strain of *Algibacter*. All pHs were maintained at 7.5 and cell yields were calculated by centrifugation 4,500 rpm for 20 min, decanting the liquor and freeze drying the cell pellet.

TABLE 3

Comparison of culture media in g/L composition used in the biomass optimisation of *Algibacter* sp. AQP096

| Media | a (g/L) | b (G/L) | c (G/L) | d (G/L) | e (G/L) | f (G/L) |
|---|---|---|---|---|---|---|
| Glucose | | 1 | 1 | | 33 | 1 |
| Peptone | 5 | | | | | |
| Yeast Extract | 1 | 5 | 5 | | 45 | 15 |
| TSB | | | | 30 | | |
| Vegetable oil | | | | | | 100 μL/ml |
| Imidazole | | | | | | 20 mMol |
| Mendadione | | | | | | 100 μg/ml |
| Lipase | | | | | | 0.05 ml/L |
| Phosphate | | | 2.5 | | 2.5 | 2.5 |
| Na Acetate | | | | | | 0.1 ml/L |
| Natural sea water | 1 L | 1 L | 1 L | 1 L | 1 L | 1 L |

The results are shown in table 4:

TABLE 4

Overview of the data of biomass optimisation of the *Algibacter* sp. AQP096 wild type and mutant strain at 5L fermentation.

| MEDIA CODE | CAROTENOID PRODUCED | PURITY OF CAROTENOID | mg/g dry weight carot | cdw Biomass g/L | lARGEST SCALE MADE (l) | Fermentation time (Hr) |
|---|---|---|---|---|---|---|
| A Low Nutrient | Zeaxanthin | 98% | 3.47 mg/g | 1.5 | 5 | 48 hr |
| B High Nutrient | Zeaxanthin | 95 | 1 mg/g | 6 | 5 | 48 hr |

TABLE 4-continued

Overview of the data of biomass optimisation of the *Algibacter* sp.
AQP096 wild type and mutant strain at 5L fermentation.

| MEDIA CODE | CAROTENOID PRODUCED | PURITY OF CAROTENOID | mg/g dry weight carot | cdw Biomass g/L | lARGEST SCALE MADE (l) | Fermentation time (Hr) |
|---|---|---|---|---|---|---|
| C High Nutrient Fed Batch | Zeaxanthin | 95 | 3.47 mg/g | 8 | 5 | 48 hr |
| D TSB | Lycopene | 95 | 3.47 mg/g | 12 | 5 | 48 hr |
| E Super High Nutrient | Zeaxanthin | 95 | 3.47 mg/g | 12 | 5 | 48 hr |
| F Super High Nutrient Using Mutant strain | Lycopene | 95 | 10.41 mg/g | 12 | 5 | 48 hr |

The initial experiments using the marine bacterium *Algibacter* strain NCIMB AQP096 produced a zeaxanthin yield of 3.47 mg/g dry biomass with a total zeaxanthin titre per L of 5.61 mg/L (see table 4).

Early medium optimisation studies have demonstrated an increased biomass from 1.05 g/l to 12 g/l cell dry weight (cdw) using Media F. The isolation of an over producing zeaxanthin strain of AQP096 has improved the yield of zeaxanthin titre to over 125 mg/L when cultured using media F (see table 4)

Example 4

Classical Strain Mutagenesis to Isolate Zeaxanthin Overproducing Mutants of AQP096

The aim of this experiment was to increase zeaxanthin yield per unit biomass by generating UV-induced mutations in AQP096 that result in highly pigmented strains (strains that overproduce zeaxanthin so that levels are higher than those in the wild type strain).

An overnight inoculum culture of AQP096 was diluted 100-fold into fresh marine broth and grown to a cell density of approximately 2×109 to 5×109 cells per ml. The cells were washed (by centrifugation) in sterile seawater and then resuspended in sterile seawater at ~2×109 cells per ml. 0.1 ml aliquots of 10-5 dilutions were plated out in duplicate on solid media to provide a non-irradiated control.

6 ml aliquots of the cell suspension were transferred into 20 sterile Petri dishes. All irradiation of cell cultures was conducted using a laminar flow biosafety cabinet. The UV function within the biosafety cabinet (UV tube emitting at 254 nm) was switched on to irradiate the cell suspensions for the following periods: 15 seconds, 30 seconds, 60 seconds, 90 seconds, 2 minutes, 4 minutes, 6 minutes, 8 minutes, 10 minutes, 12 minutes, 15 minutes, 18 minutes, 20 minutes, 22 minutes, 25 minutes, 28 minutes, 30 minutes, 45 minutes, 60 minutes and 90 minutes.

After irradiation, 1 ml aliquots of irradiated cells were diluted serially in sterile seawater to 10-5. 0.1 ml aliquots of the dilutions were plated out in duplicate onto marine agar. In addition, 1.0 ml aliquots of (undiluted) irradiated cells were diluted into 20 ml volumes of fresh marine broth and cultured overnight. The cultures were then serially diluted to 10-5 and 0.1 ml aliquots of the dilutions were plated out in duplicate onto marine agar media.

All plates were inverted and incubated at room temperature for five days before being examined for any highly pigmented colonies.

Colonies that appeared to be highly pigmented orange/yellow (or even slightly different in colour from the non-irradiated control) were picked off and streaked out onto fresh marine agar plates alongside the control. Carotenoid analysis was then conducted using standard HPLC analysis and concentration of zeaxanthin measured according to the above-mentioned formula.

Classical strain mutagenesis yielded 2 mutants of AQP096 that displayed improved or different carotenoid profiles. This data is summarised in table 5.

TABLE 5

Mutant strains of AQP096 isolated from the classical mutagenesis of AQP0096 using UV irradiation to isolate zeaxanthin overproducing mutants.

| strain id | Major CAROTENOID PRODUCED | % OF TOTAL CAROTENOID | mg/g dry weight | lARGEST SCALE MADE (l) | Fermentation time (Hr) |
|---|---|---|---|---|---|
| AQP096 Wild Type | Zeaxanthin | 98% | 3.47 mg/g | 5 | 48 hr |
| AQP096-16 | Zeaxanthin | 98% | 11.41 mg/g | 5 | 48 hr |

The mutant strain AQP096-16 has been deposited under Budapest Treaty (Accession No. NCIMB 41383).

Example 5

The Production of Lycopene from Strain AQP096 Using Carotenoid Biosynthetic Control Regulators and Altering the Carbon to Nitrogen Ratio During Fermentation When cultured in Tryptone Soy Broth (TSB), cultures of AQP096 were observed to produce a pink red colouration instead of the more usual yellow orange colour when cultured using standard marine broth. Analysis of the pigments by HPLC (See FIGS. 3a and 3b) showed that the major carotenoid produced by AQP096 when cultured in TSB was lycopene.

Further studies demonstrated that the production of lycopene could be controlled in AQP096 by the careful regulation of the carbon to nitrogen ratio in the culture medium. This lycopene control mechanism could be further regulated with the addition of carotenoid biosynthesis regulators, imidazole (5 mM) and casamino acid (12.5 g.l).

TABLE 6

The regulation of lycopene production using peptone as a carbon source to block conversion of lycopene to zeaxanthin

| Carbon source | 1 g/l of peptone | 1 g/l of peptone | 1 g/l of peptone | 1 g/l of peptone | 1 g/l of peptone |
|---|---|---|---|---|---|
| Nitrogen source | 2 g/l of yeast extract | 5 g/l of yeast extract | 10 g/l of yeast extract | 15 g/l of yeast extract | 30 g/l of yeast extract |
| % Zeaxanthin of total carotenoid | 98 | 98 | 90 | 70 | 40 |
| % Lycopene of total carotenoid | 2 | 2 | 10 | 30 | 60 |

TABLE 7

The regulation of lycopene production using Glucose as a carbon source to block conversion of lycopene to zeaxanthin

| Carbon source | 1 g/l of Glucose | 1 g/l of Glucose | 1 g/l of Glucose | 1 g/l of Glucose | 1 g/l of Glucose |
|---|---|---|---|---|---|
| Nitrogen source | 2 g/l of yeast extract | 5 g/l of yeast extract | 10 g/l of yeast extract | 15 g/l of yeast extract | 30 g/l of yeast extract |
| % Zeaxanthin of total carotenoid | 98 | 80 | 50 | 45 | 10 |
| % Lycopene of total carotenoid | 2 | 20 | 50 | 55 | 90 |

Example 6

The Induction of the Carotenoid Biosynthetic Pathway Using Menadione

Menadione at a concentration of 0.100 mg/ml was added to a 24 hr old culture of AQP096 cultured in marine broth. This culture was further incubated for 4 days on the orbital shaker at 220 rpm for 24 hours.

After 5 days of incubation, cultures were centrifuged (4,500 rpm, 20 min) and the pigments analysed for carotenoid content by HPLC (See FIGS. 4a and 4b). Results demonstrated that menadione induced the production of all carotenoids associated with the standard carotenoid biosynthetic pathway in strain AQP096.

Under standard growth conditions, strain AQP096 produces 98% pure zeaxanthin. The use of menadione reduces the amount of zeaxanthin produced by AQP096 to around 60% of zeaxanthin. However, menadione induced the production of about 10% of beta carotene, 6% of lycopene, 8% beta-cryptoxanthin, 12% of canthaxanthin, 12% astaxanthin and 2% other carotenoids such as adonirubin and 3-hydroxyechinenone.

Example 7

The Production of Phytoene and Phytofluene from Cultures of AQP096

Usually isolated from plants and microorganisms grown in the presence of desaturation inhibitors, the inventors have managed to obtain a colourless mutant (mutant 026) which produces phytoene as major carotenoid.

HPLC analysis of both the coloured wild type strain and colourless mutant strains of AQP096 for phytoene showed the presence of the colourless carotenoids phytoene and phytofluene at a total concentration of 2 mg/g. Phytoene is the precursor of carotenoid biosynthesis in many organisms (see FIG. 5).

Phytoene and phytofluene were measured by HPLC using a solvent system of 80% acetonitrile, 10% methanol and 10% H20 with a run time of 20 minutes, isocratic at measuring at a wavelength of 285 nm at a flow rate of 1 ml/min.

The invention claimed is:

1. A method for producing a carotenoid or pre-carotenoid wherein the carotenoid or pre-carotenoid is zeaxanthin, lycopene, 3'-hydroxyechnenone, β-cryptoxanthin, β-carotene, phytoene and/or phytofluene comprising the steps of:
   a) culturing bacteria from the genus *Algibacter* sp, in a suitable culture medium under conditions and for a time period suitable for production of said zeaxanthin, lycopene, 3'-hydroxyechnenone, β-cryptoxanthin, β-carotene, phytoene and/or phytofluene; and
   b) recovering said zeaxanthin, lycopene, 3'-hydroxyechnenone, β-cryptoxanthin, β-carotene, phytoene and/or phytofluene from the bacteria.

2. The method of claim 1, wherein the culture medium comprises menadione, casamino acid and/or imidazole for carotenoid bio-synthesis regulation.

3. The method according to claim 1, wherein the *Algibacter* sp. is a marine species.

4. The method according to claim 1, wherein the *Algibacter* species produces zeaxanthin in a greater proportion than any other carotenoid or pre-carotenoid.

5. The method according to claim 1, wherein the *Algibacter* species is as deposited at the NCIMB and identified by accession number NCIMB41268 or a mutant or a variant thereof having the property of producing zeaxanthin, lycopene, 3'-hydroxyechnenone, β-cryptoxanthin, β-carotene, phytoene and/or phytofluene.

6. The method according to claim 5, wherein the mutant is deposited at the NCIMB and identified by accession number NCIMB41383.

7. A method of preferentially producing and/or enhancing production of a particular carotenoid, comprising the steps of:
   a) culturing bacteria from the genus *Algibacter* sp in a suitable culture medium under conditions and for a time period suitable for production of said carotenoid, wherein said carotenoid is zeaxanthin, lycopene, 3'-hydroxyechnenone, β-cryptoxanthin, and/or β-carotene;
   b) measuring the level of zeaxanthin, lycopene, 3'-hydroxyechnenone, β-cryptoxanthin, and/or β-carotene produced in comparison to other carotenoids produced; and
   c) culturing said bacteria under different conditions to those adopted under a) above and measuring and comparing the level of zeaxanthin, lycopene, 3'-hydroxyechnenone, β-cryptoxanthin, and/or β-carotene produced to determine which, if any, of zeaxanthin, lycopene, 3'-hydroxyechnenone, β-cryptoxanthin, and/or β-carotene are preferentially produced and/or exhibit enhanced production under said different conditions.

8. The method according to claim 7, wherein step c) is repeated as necessary in order to identify suitable culture conditions for preferential and/or enhanced levels of production of zeaxanthin, lycopene, 3'-hydroxyechnenone, β-cryptoxanthin, and/or β-carotene.

9. The method according to claim 7, wherein the conditions are altered by controlling the ratio of carbon to nitrogen in the culture medium.

10. The method according to claim 7, wherein the carotenoid is zeaxanthin.

11. The method according to claim 7, wherein the *Algibacter* species is as deposited at the NCIMB and identified by accession number NCIMB41268 or a mutant or a variant thereof having the property of producing zeaxanthin, lycopene, 3'-hydroxyechnenone, β-cryptoxanthin, and/or β-carotene.

12. The method according to claim 11, wherein the mutant is deposited at the NCIMB and identified by accession number NCIMB41383.

13. A method of preferentially producing and/or enhancing production of a particular carotenoid or pre-carotenoid, comprising the steps of:
   a) culturing bacteria from the genus *Algibacter* sp in a suitable culture medium under conditions and for a time period suitable for production of said carotenoid or pre-carotenoid, wherein said carotenoid or pre-carotenoid is zeaxanthin, lycopene, 3'-hydroxyechnenone, β-cryptoxanthin, β-carotene, phytoene and/or phytofluene;
   b) measuring the level of zeaxanthin, lycopene, 3'-hydroxyechnenone, β-cryptoxanthin, β-carotene, phytoene and/or phytofluene; produced in comparison to other carotenoids produced; and
   c) subjecting said bacteria to mutagenisis and culturing said mutagenised bacteria under the same conditions employed in a); and
   d) measuring and comparing the level of zeaxanthin, lycopene, 3'-hydroxyechnenone, β-cryptoxanthin, β-carotene, phytoene and/or phytofluene produced to determine which, if any, of zeaxanthin, lycopene, 3'-hydroxyechnenone, β-cryptoxanthin, β-carotene, phytoene and/or phytofluene are preferentially produced and/or exhibit enhanced production as a result of the mutagenisis.

14. The method according to claim 13, wherein step c) is repeated as necessary in order to identify suitable culture conditions for preferential and/or enhanced levels of production of zeaxanthin, lycopene, 3'-hydroxyechnenone, β-cryptoxanthin, β-carotene, phytoene and/or phytofluene.

15. The method according to claim 13, wherein the carotenoid is zeaxanthin.

16. The method according to claim 13, wherein the *Algibacter* sp. is as deposited at the NCIMB and identified by accession number NCIMB41268 or a mutant or variant thereof having the property of producing phytoene, phytoflune, 3'-hydroxyechnenone, β-cryptoxanthin, β-carotene, zeaxanthin and/or lycopene.

17. The method according to claim 16, wherein the mutant is deposited at the NCIMB and identified by accession number NCIMB41383.

18. A bacteria deposited at the NCIMB and identified by accession number NCIMB41268, or a mutant identified by accession number NCIMB 41383 or variant thereof having the property of producing phytoene, phytofluene, 3'-hydroxyechnenone, β-cryptoxanthin, β-carotene, zeaxanthin and/or lycopene.

* * * * *